United States Patent [19]
Atkins

[11] Patent Number: 5,775,903
[45] Date of Patent: Jul. 7, 1998

[54] ENDODONTIC INSTRUMENT WITH A HUGGER HANDLE

[76] Inventor: John Atkins, 3542 N. Albany, Chicago, Ill. 60618

[21] Appl. No.: 772,628

[22] Filed: Dec. 23, 1996

[51] Int. Cl.$^6$ ............................................. A61C 5/02
[52] U.S. Cl. ............................................. 433/102
[58] Field of Search ............................ 433/102, 141; 81/177.1

[56] References Cited

U.S. PATENT DOCUMENTS

| | | | |
|---|---|---|---|
| 4,044,468 | 8/1977 | Kahn | 433/102 |
| 4,280,808 | 7/1981 | Johnsen et al. | 433/141 |
| 4,321,040 | 3/1982 | Miller et al. | 433/102 |
| 4,824,369 | 4/1989 | Levy | 433/102 |
| 4,836,780 | 6/1989 | Buchanan | 433/102 |
| 4,859,183 | 8/1989 | Martin | 433/102 |
| 5,498,158 | 3/1996 | Wong | 433/102 |
| 5,516,287 | 5/1996 | Zdarsky | 433/102 |

*Primary Examiner*—John J. Wilson
*Attorney, Agent, or Firm*—Hill & Simpson

[57] ABSTRACT

An endodontic instrument has a comfortable grip especially for use for a long time of period. A handle of the endodontic instrument includes a cylindrical stem, opposite end portions, and plural brims radially extending from the circumferential surface of the stem in a plate shape juxtaposed in the axial direction of the stem with a predetermined space. When an operator grips the handle of the endodontic instrument, the operator's fingers can readily control the handle through contacts to the brims while the brims engage the bulges of the fingers adequately. The brim preferably has recesses to provide the identification of the instrument's orientation in the finger and also can preferably be made of a resilient material to make the contacts softer to provide better blood flow in finger tips and providing less finger tip stress.

17 Claims, 2 Drawing Sheets

ENDODONTIC INSTRUMENT WITH A HUGGER HANDLE

BACKGROUND OF THE INVENTION

1. Field of the Invention

This invention relates to an endodontic instrument such as a file, a reamer, a barbed broach, a plugger, a spreader, a condenser, and the like and, more particularly, to an endodontic finger instrument manipulated by the thumb and index finger of a dentist for intracanal therapy.

2. Description of Related Art

In intracanal therapy, dentists are sometimes required to manipulate an endodontic hand instrument or finger instrument, such as files, reamers, and the like, to shape, scrape, ream or abrade the wall of root canal to be treated. During such therapy, those hand instruments are gingerly moved in and out and rotated one way or another to shape the wall of the root canal, which is generally curved and narrowed. Those endodontic instruments are usually constituted of a handle to be gripped by fingers and a tool portion having teeth, barbs, flutes, edges, or the like. To control the endodontic instruments, the handle is gripped normally by thumb and index finger of the dentist. Grip and tactile feel of dentists' fingertips is therefore essential for optimum control of those endodontic instruments.

The contours of the handles of those endodontic instruments can be classified into two groups: cylindrical shape and peanut shape of varying cross-sectional configurations. A ribbed cylinder shaped handle is disclosed in U.S. Pat. No. 4,859,183. The handle is formed with spaced cylindrical portions, or ribs, having grooves located between the cylindrical portions which go completely around the handle or may only be on a flat side. The peanut shape handles are more common, e.g., as disclosed in U.S. Pat. Nos. 4,280,808, 4,044,461, and 4,824,369. In those patents, the surface of handle is relatively concave to fit the bulge of fingers while the opposite ends of the handle are formed to radially enlarged.

On the surface of such handles, some structure provides anti-slipping functions. Grooves may be formed on a cylindrical surface (see, '183 patent above) or a conical surface (see, '808 patent above) as to round the handle. Grooves are sometimes formed to extend in an axial direction of the handle. Grids, in which one set of grooves parallel extending around the handle intersect another set of grooves parallel extending perpendicularly to the former set of the grooves, may be formed on the surface of the handle. Moreover, since the endodontic instruments are not only moved in and out but also rotated within the curved root canal, the endodontic instruments sometimes have a face or faces on their handle to identify to the touch the rotational orientation of the endodontic instruments attached to the handle. Protuberances or recesses can be formed on the surface of the handle (see, '468 patent above) to identify a face on the handle.

However, those conventional handles of endodontic instruments are not suitable for dentists to use them for a long period of time. After using such endodontic instruments for hours, dentists become fatigued and lose their gripping force and precise control. When the dentists grip those endodontic instruments with weak gripping force, the dentist likely lose their fingertips feeling on the instrument, thereby tending to lose dexterous control over the instruments. The length of the handle of prior art files has generally been 8 to 9 millimeters (see '461 patent), and applicant has found that such length is inadequate for full control. Prolonged use of such instruments may raise a problem of carpel tunnel syndrome, which may also cause the dentists to lose their delicate control over the instruments.

SUMMARY OF THE INVENTION

It is an object of the invention to provide an endodontic instrument suitable for use for longer periods of times maintaining good controllability thereof even when gripped with weak gripping force by the dentists.

The endodontic instrument according to the invention includes an intracanal tool portion to shape a wall of the root canal of a patient, and a handle having a stem axially extending and supporting one end of the intracanal tool portion, opposite end portions formed on the both ends of the stem, and a plurality of brims radially extending from the circumferential surface of the stem in a disc or plate shape, juxtaposed in the axial direction of the stem with a predetermined space form one another between the end portions. When an operator grips the handle, only circumferential edges of the brims are in contact with the fingers of the operator, and therefore feelings at the fingertips of the operator remain even when the handle is gripped with weaker force. The length of the handle is very long, preferably, in the range of 11 to 13 millimeters to assure fingers control under all circumstances.

According to a preferred embodiment of the invention, the brims so radially extend that the brims located closer to the center of the handle in the axial direction of the stem have a radially shorter size so as to fit a convex bulge of the finger. The predetermined space is a space such that when the operator grips the handle the surfaces of the fingers remained spaced away from the circumferential surface of the stem.

In another aspect of the invention, each brim has a plurality of recesses, or notches circumferentially spaced, with the circumferential edge of each brim, at the recesses, spaced away from the finger of the operator when the operator grips the handle. The brims may be in a rotationally symmetric shape having the center axis of the stem as a symmetry axis for easy recognition of face orientation of the handle and aiding in tactile recognition of the amount of rotary movement, in degrees, in either direction of rotation in the fingers.

While the brim can be made of metal material an important feature of my preferred handle is to employ resilient material such as a resin material that flexes, but returns to its undeflected state when released. The brims, the end portions, and the stem can be formed in a united body. When the brims are made of a resilient material, the flexibility of the resilient material allows the operator to readily grip the handle of the endodontic instrument with soft contact.

BRIEF DESCRIPTION OF THE DRAWINGS

The above and other objects and features of the invention are apparent to those skilled in the art from the following preferred embodiments thereof when considered in conjunction with the accompanied drawings, in which:

FIGS. 7, 8 are illustrations showing endodontic instruments whose handle is made of either metal material (in FIG. 7) or resin material plastic (in FIG. 8) according to the invention when the instrument is gripped by fingers of an operator.

DETAILED DESCRIPTION OF THE PREFERRED EMBODIMENTS

Figure 1:
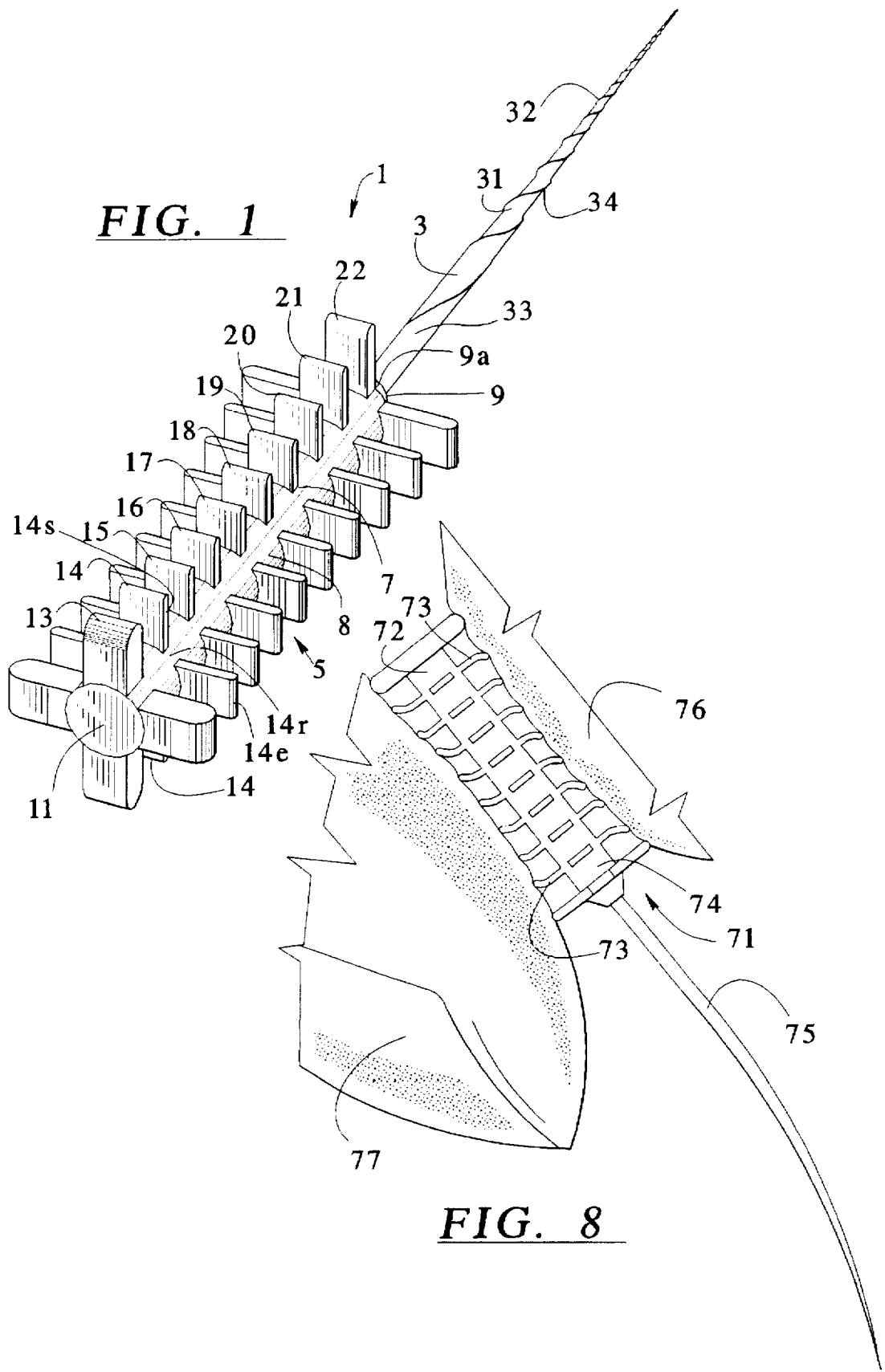
FIG. 1 is a perspective view showing an endodontic instrument according to a preferred embodiment of the invention.

Referring to the drawing in detail in particular, to FIGS. 1 to 4, an endodontic hand file used for intracanal therapy is shown. The endodontic hand file 1 is handled by fingers of an operator, such as a dentist. The endodontic hand file 1 is constituted of a tool portion 3 serving as a file, and a handle 5 to be gripped and controlled normally by the thumb and index finger of the operator.

The tool portion 3 is extending in an axial direction in a length suitable for intracanal treatment and made in a tapered shape having a smaller diameter at a distal end, or a working end 31, and a larger diameter at a proximal end, or a shank end 33. The working end 31 has cutting edges 34 and flutes 32 extending on the conical surface of the tool portion 3 in a helix shape so as to scrape the wall of the root canal when the file 1 proceeds in the root canal during the intracanal therapy. Although in this embodiment, the tool portion 3 is made to operate as a file, this invention is applicable to any other endodontic hand instrument, such as a barbed broach, a reamer, a plugger, a spreader, a condenser, and any other endodontic hand or finger instrument conceivable to a person skilled in the art of endodontic instruments. The tool portion 3 is made of a metallic material ordinarily used for endodontic instruments of this type.

The handle 5 is particularly designed to provide comfortable control when the operator uses the endodontic hand file 1 for a long period of time. The handle 5 is also designed to create excellent control when the operator rotates the endodontic hand file 1. The handle 5 is constituted of a cylindrical stem 7 extending an axial direction thereof, a pair of end portions 9, 11 of the stem 7, and a plurality of brims 13 to 22. The handle 5 may be made of a metallic material. However, the handle 5 may, preferentially, be made of a resilient resin material as specifically described below. The stem 7, the end portions 9, 11, and the brims 13 to 22 are made in a united body of the same material, but those parts can be made separately or even separately made of different materials and assembled later. To protect the surface of the handle 5, some proper resin may be applicable on the surface of the handle 5 as long as it does not lose the function of the handle 5.

The stem 7 has a substantially cylindrical shape. The stem 7 extends between the opposite end portions 9, 11 in the axial direction in a length suitable to handled by the thumb and index finger of operators. The stem 7 of this embodiment has a length L of about a half inch, preferably in the range of about 0.43 to 0.5 inches. The length of the stem 7 can be changed depending on kinds of endodontic instruments but it is important to have a length well over the conventional 0.3 to 0.35 inches as noted above. The stem 7 has a diameter substantially smaller than conventional files, and in this embodiment, the stem 7 has the diameter of around .095 inch. The brims 13 to 22 are arranged on a circumferential surface 8 of the stem 7.

Figure 2:
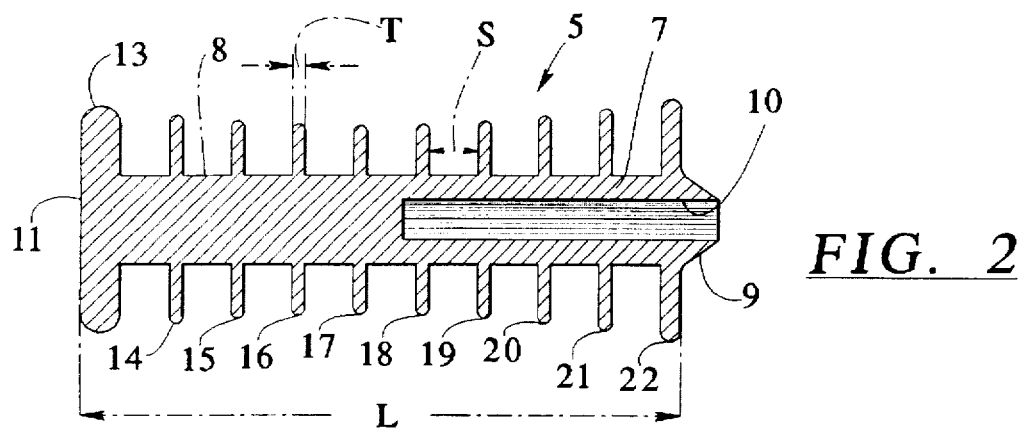
FIG. 2 is a cross section showing a handle of the endodontic instrument shown in FIG. 1.
Figure 3:
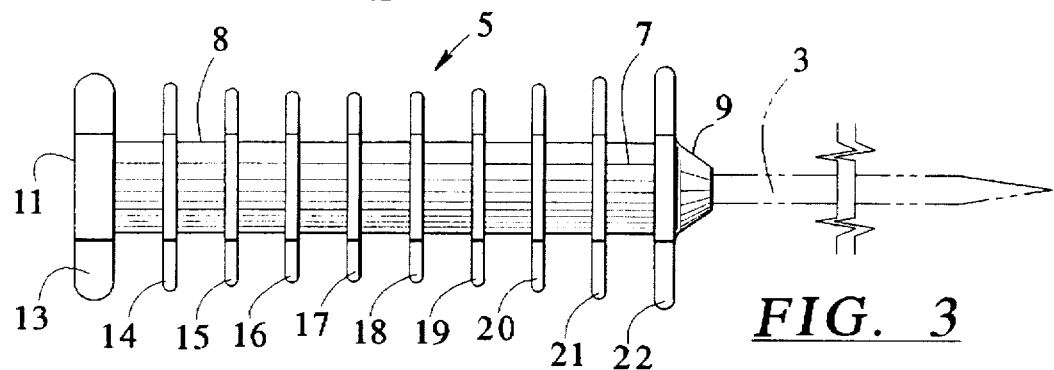
FIG. 3 is a side view showing the endodontic instrument shown in FIG. 1.

The end portion 9 of the stem 7 serves as a joint portion of the handle 5 and the tool portion 3. The end portion 9 has a hole 10 molded in place extending in the axial direction of the handle 5 at the center of the end portion. The hole 10 extends nearly up to a half of the length of the stem 7 as shown in FIG. 2. The hole 10 has a diameter substantially equal to the diameter of the shank end 33. Preferably the shank end 33 of the tool portion 3 is insert molded in place in the hole 10, to be secured immovably and to extend in the same direction as the center axis of the handle 5. The end portion 9 has a tapered surface 9a on the side of the tool portion 3. The other end portion 11 is contrarily, flat and has no hole.

The brims 13 to 22 serve as a grip of the handle 5 and an indicator of face orientation of the file 1, and in use, an indicator of how far the file has rotated in degrees. In this embodiment, ten brims 13 to 22 are provided to create a comfortable grip of the handle 5. Each brim 13 to 22 is radially extending from the circumferential surface 8 of the stem 7. Each brim 13 to 22 is in a plate shape having substantially same thickness between at a radially inward portion thereof and at a radially outward portion thereof or in a plate shape that the radially outside portion of the brims 13 to 22 can be formed with a slightly thinner thickness than the radially inward portion of the brims 13 to 22 to effectuate the fabrication of this handle 5. The thickness of the brims 13 to 22 is measured in the axial direction of the stem 7 as shown by numeral T in FIG. 2. The brims 13, 22 located closest to the end portions 9, 11 have a thickness thicker than the thickness of the brims 14 to 21. In this embodiment, the brims 14 to 21 have the thickness of about 0.015 to 0.020 inches at the base and about 0.01 inches at the outer perimeter, while the brims 13, 21 have the thickness of about twice that. The ten brims 13 to 22 are juxtaposed in the axial direction of the stem 7 with a predetermined space S form one another between the end portions 9, 11. The space S is substantially larger than the thickness T and is about 0.040 inch, which is designed twice or larger than the thickness T in this embodiment. The space S between the two brims next to each other is a constant size in this embodiment. As a modification, however, the space S may be designed to be different depending on the location on the circumferential surface 8.

The brims 13 to 22 radially extending have different lengths in the radial direction to fit the bulges of the fingers of operators. The brims 13 to 22 so radially extend that the brim located closer to the center of the handle 5 in the axial direction of the stem 7 has a radially shorter size as to fit a convex bulge of the fingers. In this embodiment, accordingly, the brims 17, 18 have the shortest radial size; the brims 16, 19 have the second shortest radial size; the brims 15, 20 have the intermediate radial size; the brims 14, 21 have the second longest radial size; the brims 13, 22 have the longest radial size. Those radial sizes are not so restricted and can be altered so as to fit the bulge of the fingers of operators. As far as the outline of those brims 13 to 22 is in a concave shape in which the sizes of the brims are gradually changing between the brims next to each other, the brims 13 to 22 are capable of serving as a comfortable grip. For example, the fourth brim 19 located at the fourth place from the side of the tool portion 3 can be radially shorter than the fifth brim 18. Moreover, if not ten but nine brims are formed on the circumferential surface 8 of the stem 7, the sizes of the brims can be, from the side of the tool portion 3, as an example: 0.230 inch, 0.182 inch, 0.160 inch, 0.152 inch, 0.158 inch, 0.164 inch, 0.172 inch, 0.180 inch, and 0.185 inch. The brim 22 can be made radially larger than the brim 13.

Figure 4:
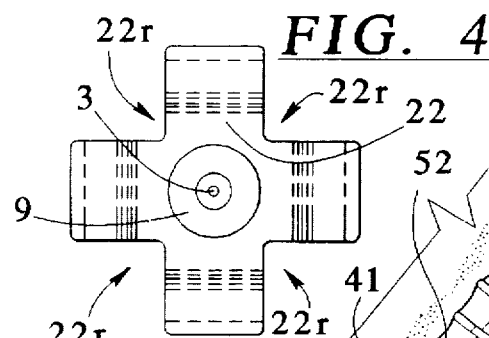
FIG. 4 is a front view showing the endodontic instrument shown in FIG. 1.

Each brim 13 to 22 has plural recesses circumferentially spaced on the circumferential edge of the brim. In FIG. 1, the brim 14, as a representative of other brims 13, 15 to 22 for simplifying their description, has four recesses 14r, which are circumferentially spaced on the circumferential edge 14e of the brim 14. When seen in the axial direction of the stem 7, the brim 22 is radially extending in a cross shape as shown in FIG. 4. The four recesses 14r (22r) divide the brim 14(22) into four portions each having a rectangular shape when seen in the axial direction. Each recess 14r(22r) has relatively flat side walls 14s angled with about 90 degrees. At the bottom of the side walls 14s, the recess 14r reaches the circumferential surface 8. The four recesses of the brims 13 to 22 are located in the same way at each brim. The brims 13 to 22 have a rotationally symmetric shape having the center axis of the stem 7 as a symmetry axis. In this embodiment, when the handle 5 is rotated by 90 degrees, the brims 13 to 22 return to the same position as the original position. The recess 14r as well as other recesses of the other brims 13, 15 to 22 make the circumferential edge of each brim away from the fingers of the operator. That is, when the operator grips the handle 5 by the thumb and the index finger, the operator feels contacts of the circumferential edges of the brims 13 to 22 but does feel nothing at recesses of the brims 13 to 22. The circumferential edges of the brims 13 to 22 are relatively flat but chamfered to avoid the fingertips to be injured.

Figure 7:
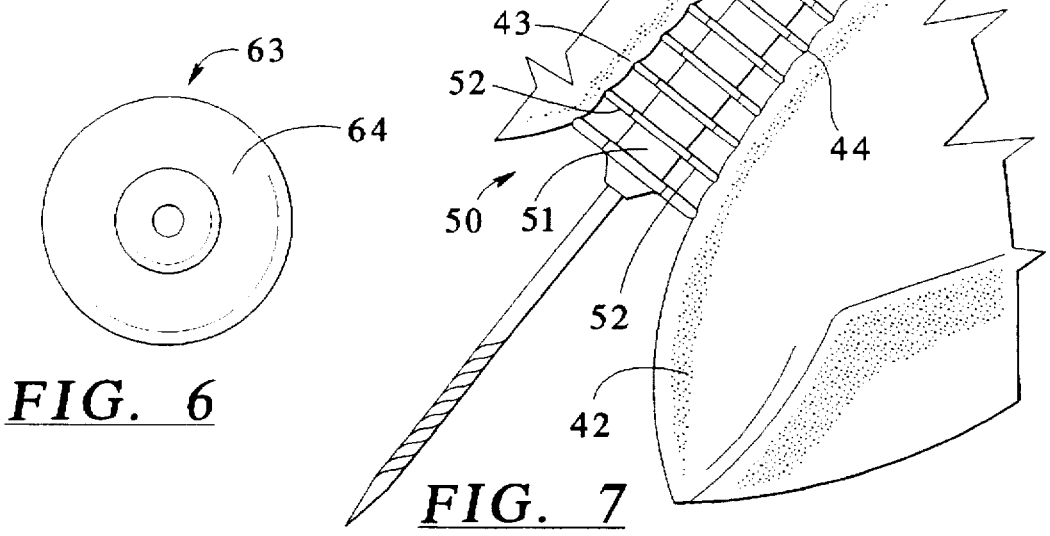

FIG. 7 shows a situation that the endodontic hand file 1a is gripped by fingers 41, 42. The brims 52 are radially extending from the circumferential surface of the stem 51. The bulges 43, 44 of the fingers 41, 42 are in contact with the surfaces of the brims 52 of the endodontic hand file 1a. When the handle 50 is gripped by the fingers 41, 42 with normal force to grip the file 1a, the circumferential edges of the brims 52 come to push the surface of the fingers 41, 42, thereby making the surface of the fingers 41, 42 corrugated. That is, each brim 52 engages the surface of the fingers sufficiently, so that even when the operate loses his gripping force due to fatigue, the endodontic hand file 1a still allows the fingers 41, 42 to control the file 1a desirably. Accordingly, the operator can use the endodontic hand file 1a for longer periods of time with minimal stress and without tiring finger muscles. The endodontic hand file 1a is also designed to rotate laterally and being oriented as to the amount of rotation. For removal of pulp, tissue, and debris, the endodontic hand file 1a can be rotated by, for example, 90 degrees each way. Since each brim 52 has a cross shape likewise shown in FIG. 4, the operator can easily recognize the orientation of the hand file 1a even while rapidly rotating the hand file 1a or even when fingertips' sense becomes dull due to fatigue.

Figure 5:
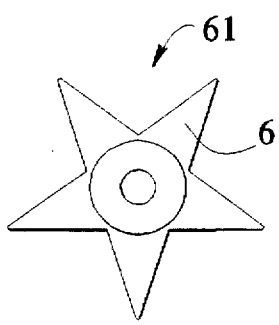
FIGS. 5, 6 are front views showing other endodontic instruments according to preferred embodiments of the invention.
Figure 6:

Referring to FIGS. 5, 6, modifications of the endodontic hand file are shown. In FIG. 5, an endodontic hand file 61 has star shaped brims 62. This star shaped brims 62 are designed to rotate laterally 72 degrees each way and to be oriented by each 36 degree rotation. In FIG. 6, the endodontic hand file 63 has the brims 64 having no recess. The brim 64 is in a disc shape, so that although the operator cannot recognize the orientation of the file 63, the operator can easily rotate the file 63, which can be manufactured inexpensively in comparison with the hand files having recesses.

The handle for the endodontic tools, such as files, can be made of a resilient material, such as a resin material, rubber, or any resilient material suitable for dental treatment. A preferred embodiment has a durometer hardness of about 62 on the D scale but a satisfactory range is from about 60 to 70 on the D scale. FIG. 8 shows a situation that an endodontic file instrument 71 whose handle 72 is made of a plastic resin capable of bending when pushed and bending back when released. The handle 72 has the same shape as handle 5 shown in FIG. 1 and brims 73 extend radially from a stem 74. A curved tool portion 75 useful in preventing lodging in curved canal work is immovably secured at the one end portion of the stem 74. In this embodiment, each brim 73 extends in a plate shape when the handle 72 is not gripped. When the handle 72 is gripped by fingers 76, 77, the tips of the brims 73 are bent according to the gripping force. When the fingers 76, 77 lose the grip, the brims 73 can be readily bend back. This structure of the brims 73 brings soft and comfortable contact with the fingers. The operator also can adequately grip the handle 72 with less pressure on the handle 72. Accordingly, the operator can use the endodontic hand file 71 for long period of time; gloves of the operator may not be torn; the fingers 76, 77 can avoid to be blistering.

The foregoing description of preferred embodiments of the invention has been presented for purposes of illustration and description, and is not intended to be exhaustive or to limited the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not to be limited by the specification, be defined by the claims set forth below.

I claim:

1. An endodontic instrument for root canal therapy handled by fingers of an operator, comprising:

intracanal tool portion for operating a wall of the root canal having a working end to be inserted into the root canal and a shank end, and a handle manually handled by the thumb and the index finger of the operator comprising:

a stem extending in an axial direction thereof in a substantially cylindrical shape formed with a circumferential surface and a pair of opposite ends, one of the ends having a recess extending in the axial direction of the stem immovably securing the shank end of the intracanal tool portion therein; and a pair of end portions radially extending from the opposite ends of the handle member; and a plurality of brims radially extending from the circumferential surface of the stem in a plate shaped juxtaposed in the axial direction of the stem with a predetermined space from one another between the end portions, wherein the brims are in a rotationally symmetric shape having the center axis of the stem as a symmetry axis, each brim having a plurality of recesses circumferentially spaced and wherein the recesses on each brim are provided at four positions equally separated from each other on the circumferential edge of the brim such that the brim radially extends in a cross shape.

2. The endodontic instrument according to claim 1, wherein the brims so radially extend that the brims located closer to the center of the handle in the axial direction of the stem have a radial size shorter than brims at the ends so as to fit a convex bulge of the finger.

3. The endodontic instrument according to claim 1, wherein the stem, the end portions, and the brims are made as a united body.

4. The endodontic instrument according to claim 1, wherein the stem, the end portions, and the brims are made of a resilient material.

5. The endodontic instrument according to claim 1, wherein the material is a plastic resin.

6. The endodontic instrument according to claim 1, wherein the stem, the end portions, and the brims are made of a resilient material having a durometer hardness of about 62 on the Rockwell D scale.

7. The endodontic instrument according to claim 1, wherein the handle has an overall length, for finger control, of 0.45 to 0.50 inches.

8. The endodontic instrument according to claim 1, wherein the recesses make the circumferential edge of each brim separated from the finger of the operator when the operator grips the handle.

9. The endodontic instrument according to claim 1 wherein the stems, the end portions and the brims are made of a resilient material having a durometer hardness of about 55 to 75 on the Rockwell D scale.

10. An endodontic instrument for root canal therapy handled by fingers of an operator, comprising:

intracanal tool portion for operating a wall of the root canal having a working end to be inserted into the root canal and a shank end, and a handle manually handled by the thumb and the index finger of the operator comprising:

a stem extending in an axial direction thereof in a substantially cylindrical shape formed with a circumferential surface and a pair of opposite ends, one of the ends having a recess extending in the axial direction of the stem immovably securing the shank end of the intracanal tool portion therein; and a pair of end portions radially extending from the opposite ends of the handle member; and a plurality of brims radially extending from the circumferential surface of the stem in a plate shaped juxtaposed in the axial direction of the stem with a predetermined space from one another between the end portions, wherein the brims are in a rotationally symmetric shape having the center axis of the stem as a symmetry axis, each brim having a plurality of recesses circumferentially spaced and wherein the recesses on each brim are provided at five positions equally separated from each other on the circumferential edge of the brim such that the brim radially extends in a star shape.

11. The endodontic instrument according to claim 10, wherein the brims so radially extend that the brims located closer to the center of the handle in the axial direction of the stem have a radial size shorter than brims at the ends so as to fit a convex bulge of the finger.

12. The endodontic instrument according to claim 10, wherein the stem, the end portions, and the brims are made as a united body.

13. The endodontic instrument according to claim 10, wherein the brims are made of a resilient material.

14. The endodontic instrument according to claim 10, wherein the material is a plastic resin.

15. The endodontic instrument according to claim 10, wherein the end portions, and the brims are made of a resilient material having a durometer hardness of about 62 on the Rockwell D scale.

16. The endodontic instrument according to claim 10, wherein the handle has an overall length for finger control, of 0.45 to 0.50 inches.

17. The endodontic instrument according to claim 10, wherein the stems, the end portions and the brims are made of a resilient material having a durometer hardness of about 55 to 75 on the Rockwell D scale.

* * * * *